United States Patent [19]

Morita et al.

[11] Patent Number: 4,735,358
[45] Date of Patent: Apr. 5, 1988

[54] METHOD AND APPARATUS OF VAPORIZING ACTIVE SUBSTANCES

[75] Inventors: Masahiro Morita, Sakai; Kiyofumi Tashiro, Amagasaki; Chikashi Eguma, Shiga; Osamu Suo, Otsu, all of Japan

[73] Assignees: Daiken Iko Kabushiki Kaisha, Osaka; Kabushiki Kaisha Fujiko, Hyogo; Shiraimatsu Shinyaku Kabushiki Kaisha, Shiga, all of Japan

[21] Appl. No.: 21,083

[22] Filed: Mar. 3, 1987

[30] Foreign Application Priority Data

Mar. 4, 1986 [JP] Japan ................................. 61-47866

[51] Int. Cl.4 ............................................. A61L 9/03
[52] U.S. Cl. .......................................... 239/1; 239/52; 239/289; 242/55.55; 206/389
[58] Field of Search ................... 239/6, 47, 48, 49, 50, 239/52, 1, 289; 242/55.55; 206/389

[56] References Cited

U.S. PATENT DOCUMENTS

| 233,072 | 10/1880 | Chellew | 239/50 |
| 2,047,089 | 7/1936 | Turner | 239/48 |
| 4,663,315 | 5/1987 | Hasegawa et al. | 239/47 |

*Primary Examiner*—Andres Kashnikow
*Assistant Examiner*—Chris Trainor
*Attorney, Agent, or Firm*—Armstrong, Nikaido, Marmelstein & Kubovcik

[57] ABSTRACT

The invention provides a method and an apparatus which assure a sustained vaporization of deodorants, perfumes, pest control agents and other substances intended to modify, condition on otherwise alter the atmosphere. A tape comprising a base material and, as supported thereon, at least one active substance which vaporizes at ambient temperature or under heating in a condition in which its vaporization is inhibited is driven relative to a head which is adapted to remove the inhibition of vaporization, whereby the active substance is vaporized at a constant rate.

16 Claims, 3 Drawing Sheets

METHOD AND APPARATUS OF VAPORIZING ACTIVE SUBSTANCES

BACKGROUND OF THE INVENTION

The present invention relates to a method and an apparatus for providing a sustained vaporization, either continuous or intermittent, of deodorants, air fresheners, perfumes, pest control agents, and other optional products intended to modify, condition or otherwise alter the atmosphere.

It is known in the art to dissolve an insecticidal agent capable of controlling noxious insects such as mosquitoes, a deodorant formulated to remove or cancel out unpleasant odors or a perfume which emits an aroma simulating that of a flower, fruit or the like in a solvent such as alcohol or water, fill a suitable container with the resulting dilute solution, and dispense it as a spray-mist as need arises.

It is also known to prepare a solid product from a formulation comprising a deodorant and/or an aromatic ingredient, a water-soluble high polymer and a gelling agent and allow the solid product to stand in a suitable container to thereby let it emanate the vapors of the deodorant and/or aromatic ingredient by spontaneous evaporation.

With regard to pesticides such as the insecticides for controlling mosquitoes and the like, there is also known and available an apparatus such that a small mat imbibed with the pest control agent is set in position on an electric heater plate and the heater plate is electrically energized to vaporize the pest control agent contained in the mat.

However, all of the above methods and apparatus have some disadvantages or others. Thus, although the application of a spray-mist achieves the desired result almost immediately after application, the effect falls off rapidly with time, thus requiring frequent spray applications which are troublesome.

The method employing a solid product containing the active ingredient is applicable only in cases where the active ingredient is a highly volatile substance and while the duration of effect is by far longer than that provided by spray application, this method has the drawback that the aroma is too intense during several days following unpackaging of the product and is too faint in the subsequent period. In other words, the rate of vaporization is inconstant.

The electric mosquito control mat, a typical product utilizing the third method, offers a sustained effect as compared with spray application but since the duration of effect is still of the order of hours, the mat must be replaced with a fresh one daily. In addition to the above trouble, this conventional device has the inherent disadvantage that whereas the vaporization of the active ingredient is more than sufficient in an initial stage following the start of heating, it gradually diminishes to provide only inadequate effectiveness.

The present invention has been accomplished to overcome the above-mentioned disadvantages of the prior art methods and devices and provides a novel method of vaporizing active substances and an apparatus for practicing the method which assure (i) a constant rate of vaporization, (ii) a controlled or programmed vaporization, and (iii) a long duration of emanation and effect of active substances.

SUMMARY OF THE INVENTION

The method for vaporizing active substances in accordance with the present invention comprises driving a tape 1 comprising a base material and, as supported thereon, at least one active substance which vaporizes at ambient temperature or under heating in a condition in which the vaporization thereof is inhibited relative to a head 2 adapted to remove the inhibition of vaporization to thereby vaporize said active substance in a position where said tape 1 contacts or approaches said head 2.

The vaporizing apparatus according to the present invention essentially comprises a tape 1 comprising a base material and, as supported thereon, at least one active substance which vaporizes at ambient temperature or under heating in a condition in which the vaporization thereof is inhibited, a head 2 adapted to remove the inhibition of vaporization thermally, physically or chemically, and a drive means 3 adapted to drive said tape 1 relative to said head 2.

DETAILED DESCRIPTION OF THE INVENTION

The present invention is described in detail.

Active substances to be vaporized

The active substance which is to be vaporized in accordance with the present invention can be any active substance that vaporizes at ambient temperature or under heating. The term 'active substance' is used herein to mean a substance or a composition of substances which is useful for modifying, conditioning or otherwise altering the ambient atmosphere. The term 'vaporization' as used herein means not only the evaporation of a substance but also the emanation and diffusion of a substance in a mist or other fine particulate form into the ambient atmosphere.

As examples of such active substances, there may be mentioned various deodorants, aromas (scents, perfumes, phytoncides, aromas for aroma therapy, etc.), biocides including antimicrobial agents, etc., pest control agents, etc., air fresheners, various attractants and repellents, rust inhibitors, spoilage control agents, drugs for absorption from the respiratory organ, skin or mucosa, and aromas for presence or realism effect. The following is a partial listing of representative substances in each category.

(a) Deodorants

A variety of essential oils, glyoxal, lauryl methacrylate, boron compounds, amine compounds and organic chlorine compounds can be mentioned. Particularly useful are fractions separated from plants such as those of the families Ternstroemiaceae (Theaceae), Labiatae (Lamiaceae), Lauraceae, Myrtaceae, Campanulaceae and Malvaceae. More particularly, extracts or dry-distillates from plants of the family Theaceae such as *Thea sinensis* L., *Camellia sasanqua* Thunb, *Camellia japonica* L., *Cleyira ochnacea* DC. and *Ternstroemia japonica* Thunb. are useful.

The most useful deodorant is a dry-distillate of tea leaf which can be obtained, for example by distilling tea leaf in a vacuum of 20 mmHg and collecting the fraction boiling at 180° to 200° C.

(b) Aromas

Perfumes, scents or aromas are generally used in the following three ways.

(i) Perfumes These are used for the purpose of modifying the air in a living room or a car interior to create a refreshing, cozy atmosphere.

(ii) Phytoncides These are used for disinfecting forests and wooded areas.

(iii) Aroma therapy Aromas are used medically as olfactory stimuli for therapeutic purposes.

(i) Perfumes

The following animal, plant, synthetic or compound perfumes can be mentioned as examples.

Perfumes of animal origin such as musk, civet, ambergris, castreum and so on.

Perfumes of vegetable origin such as abies oil, anis oil, balsam copaiba, balsam peru, balsam tolu, bay oil, benzoin, bergamot oil, bois de rose oil, cajuput oil, calamus oil, cananga oil, capsicum, caraway oil, cardamon oil, cassia oil, Japanese cinnamon, cassie oil, cedarwood oil, chenopodium oil, oil of cinnamon ceylon, citronella oil, clove oil, clove stem oil, clove leaf oil, coriander oil, cumin oil, elemi oil, eucalyptus oil, fennel oil, galbanum oil, geranium oil, gingergrass oil, hiba oil, jasmin oil, lavandin oil, lavender oil, lemon oil, lemongrass oil, lime oil, linaloe oil, mint oil, neroli oil, nutmeg oil, oak moss oil, ocotea oil, sweet orange oil, patchouli oil, palmarosa oil, pennyroyal oil, peppermint oil, pepper, perilla oil, petitgrain oil, pimenta, pine oil, rose oil, rosemary oil, camphor oil, ho oil, clary sage oil, sandalwood oil, spearmint oil, spike oil, star anise oil, thyme oil, tonka beans, turpentine oil, vanilla, vetiver oil, ylang ylang oil and so on.

Synthetic perfumes such as amyl acetate, α-n-amyl cinnamaldehyde, isoamyl salicylate, anisaldehyde, benzyl acetate, benzyl alcohol, borneol, l-carvone, cinnamaldehyde, cinnamyl alcohol, citral, citronellal, citronellol, coumarin, cyclamen aldehyde, ethyl butyrate, ethyl propionate, ethyl vanillin, eugenol, geraniol, geranyl acetate, heliotropine, hydroxycitronellal, ionone, linalool, linalyl acetate, l-menthol, methyl ionone, methyl salicylate, musk ambrette, "Musk T", β-naphthyl methyl ether, β-phenylethyl alcohol, α-terpineol, vanillin and so on.

Various compound aromas (ii) Phytoncides

Phytoncides vary greatly in composition and they are not single substances but are compositions of various alkaloids, glycosides, organic acids, tannic acid compounds, terpenes, and so on. Among then, α-pinene, β-pinene, 1,8-cineole, Δ³-carene, myrcene, γ-terpene, imanin, arenarin, etc. have been identified by analysis.

Essential oils extracted and purified from garlic, onion, leek, white mustard, mustard, horseradish, pepper, orange, carrot, cabbage, radish and so on; leaves of broadleaf trees such as white birch, oak, eucalyptus, etc., leaves of coniferous trees such as fir, juniper, pine, etc., prune berry, poeny root, jonquil, aspen leaf and so on can also be used as phytoncides and exhibit germicidal, insecticidal and/or acaricidal (miticidal) effects.

As substances which act as bactericides, fungicides, preservatives, disinfectants, insecticides, and insect attractants or repellents, there are known eucalyptus oil, camphor oil, geranium oil, thyme oil, mint oil, clove oil, anis oil, citronella oil, bergamot oil, lemon oil, turpentine oil, thymol, eugenol, l-menthol, l-carvone, anethole, borneol, camphor, citronellic acid, ascaridole, cinnamic acid esters, benzoic acid esters and so on.

(iii) Aromas for aroma therapy

As antihypnotic aromas, essential oils (mint, eucalyptus, lemon, vervain, citronella, cajuput, sage, thyme, clove, rosemary, hyssop, basil and other oils), and, extracts (onion, garlic and other extracts), formic acid, ethyl formate, propyl formate, acetic acid esters, amyl nitrite, trimethylcyclohexanol, allyl sulfide, etc. may be mentioned.

As hypnotic aromas, essential oils (jasmin, chamomile, neroli, etc.), nonyl alcohol, decyl alcohol, phenylethyl alcohol, methyl carbonate, ethyl carbonate, etc. may be mentioned.

As anorectic aromas, mugwort oil, rosemary oil, eucalyptus oil, myrrh oil, phenylacetic acid esters, guaiacol, indole, cresol, thiophenol, p-dichlorobenzene, p-methylquinoline, isoquinoline, pyridine, organic amines, camphor, mercaptans, ammonia, hydrogen sulfide, etc. may be mentioned.

As aperitive aromas, essential oils (basil, perilla, marjoram, thyme, laurel, juniper berry, lemon, nutmeg, ginger, onion, garlic and other oils), carvone, estragole, elemol, etc. may be mentioned.

As an anti-migraine aromas, essential oils (sweet orange, lemon, bergamot, lavender, rosemary, basil, peppermint, camphor, eucalyptus and other oils), l-menthol, 1,8-cineole, etc. may be mentioned.

As smoking abstinence aromas, essential oils (sweet orange, lemon, bergamot, clove, cinnamon, nutmeg, mace, ginger and other oils), eugenol, citral, hydroxycitronellal, etc. may be mentioned.

As antiemetic and antisyncopal aromas, there may be mentioned peppermint oil, absinth oil, eucalyptus oil, rosemary oil, l-menthol, 1,8-cinerol, citral, camphor, acetic acid and its esters, and so on.

As aphorodisiac aromas, there may be used sandalwood oil, costus oil, labadanum oil, amber, musk and so on.

As libido-depressant (sexual abstinence) aromas, there may be mentioned essential oils (lavender, bergamot, lemon, marjoram, rosemary, clary sage, peppermint, basil, rose, jasmin, petitgrain, nutmeg, cinnamon, clove, mace, ginger and other oils), citral, citronellal, borneol, linalool, geraniol, nerol, rhodinol and so on.

Aromas having antidysphoria, antidepressant or hypnotic activity are useful for application in mental hospitals.

(c) Antimicrobial agents

Among said antimicrobial agents are bactericides, fungicides, bacteriostatic agents, fungistatic agents, disinfectants and so on.

In addition to the phytoncides mentioned in the section (ii) under the heading of Aromas, they may also be used halogen compounds such as α-bromocinnamaldehyde, Bronopol ® (2-bromo-2-nitro-1,3-propanediol), etc., phenol compounds such as o-phenylphenol, p-chloro-m-cresol, etc., tetrachloroisophthalonitrile, and so on. Formaldehyde and formaldehydesource substances are also useful.

(d) Moth-proofing and insecticidal agents

For example, camphor, borneol, naphthalene, paradichlorobenzene, pyrethrin, allethrin, chloropicrin, dichloropropane, bromoethane, etc. can be used.

(e) Attractants

For example, methyleugenol, anisylacetone, 4-p-acetoxyphenylbutanone-2, p-methylacetophenone, p-oxybenzylacetone, 1,2-hexadecanediol, etc. may be mentioned.

(f) Repellents

For example, cinnamyl alcohol, phenylethyl alcohol, phthalic acid esters, benzyl benzoate, propyl o-aminobenzoate, methyl anisate, menthofuran, hydroxycitronellal, etc. may be mentioned.

(g) Refreshing agents

For example, limonene, α-pinene, β-pinene, etc. may be mentioned.

(h) Rust inhibitors

For example, ammonium salts such as monoethanolammonium benzoate, etc., nitrites such as diisopropylammonium nitrite, dicyclohexylammonium nitrite, etc., and benzotriazole and its derivatives may be mentioned.

(i) Spoilage control agents

For example, 2-(4-thiazolyl)benzoimidazole may be mentioned.

(j) Drugs for absorption from the respiratory organ, skin or mucosa.

A variety of drugs which act on the human body after absorption from the respiratory organ, skin or mucosa can be used for the purposes of the present invention. Of course, such drugs may also be useful for animals.

(k) Presence (realism) effect aromas

The substances which are useful for enhancing the realism of film, television or video scenes (the scents of flowers for a scene in a flower garden, the odor of gun smoke for a battle scene, the scent of sea for a seaside scene, etc.) or music performances can also be used for the purposes of the present invention.

Base materials

As base materials for supporting the above-mentioned active substances, there may be used tapes of textile materials such as nonwoven fabric, woven fabric, knitted fabric, cord, rope, thread, and so on. Aside from such textile materials, non-textile materials such as plastic film, sheet and foamed sheet as well as metal foils can also be employed. In the case of films and sheets, monoaxially or biaxially oriented films and sheets are advantageous for many purposes.

Raw materials for use in the fabrication of textile materials include polyester fiber, polyamide fiber, acrylic fiber, polyvinyl alcohol fiber, polypropylene fiber, polyethylene fiber, polyvinyl chloride fiber, polyvinylidene chloride fiber, polyurethane fiber, fluorocarbon resin fiber, rayon fiber, various natural fibers (wool, cotton, linen, etc.), carbon fiber, carbonized fiber, glass fiber, asbestos fiber, ceramic fiber, metal fiber, and so on.

As raw materials for the fabrication of said non-textile materials, there may be mentioned polyesters, polyamides (inclusive of aromatic polyamides), polyimides, polyolefins (polypropylene, polyethylene, olefin copolymers, etc.), polyvinyl chloride, polyvinylidene chloride, polyurethane, polystyrene, cellulose derivatives, silicone, fluorocarbon resin, natural rubber, synthetic rubber, metal foils and so on.

Laminate films or other composite products manufactured from such raw materials can also be used with advantage.

Methods of supporting active substances

As the method for supporting active substances on the base materials mentioned above, such techniques as dipping, spraying, coating, printing and so on can be utilized. It is also possible to blend or otherwise incorporate an active substance in a suitable stage in the molding of a base material.

While the active substances as such may be directly supported, they are more often used in the form of compositions prepared using such appropriate additives as diluent (inorganic solvents, organic solvents, high-viscosity liquids, plasticizers, etc.), binders, fillers, stabilizers, colorants, gelling agents, thixotropic agents and so on.

It may also be advantageous to encapsulate active substances or compositions by a suitable method. Microencapsulation using a suitable microencapsulating agent may also prove advantageous.

Tape

The tape 1 is prepared by slitting an elongated base material carrying or supporting the active substance or composition to a suitable width.

The tape 1 may be a non-endless tape having a leading end and a trailing end or an endless tape fashioned in the form of a loop.

The tape 1 to be used in the practice of the present invention must be such that the active substance which vaporizes at ambient temperature or under heating is supported in a condition in which the vaporization thereof is inhibited. The term "inhibited" as used herein covers the following situations: (a) the active substance is not volatile at ambient temperature so that it does not vaporize even if no special measure is taken to prevent its vaporization and (b) although the active substance is vaporizable at ambient temperature, its vaporization has been somehow controlled or inhibited.

If the active substance is one that vaporizes only under heating, its vaporization is inhibited only when it is supported in the base material by the above-mentioned method.

On the other hand, if the active substance is one that vaporizes at ambient temperature, it will be lost as a vapor during storage or in various stages of distribution if it is merely supported in the base material. Therefore, when the active substance is one that evaporates at ambient temperature, it is preferable to protect it against vaporization by the above-mentioned encapsulation or microencapsulation method or seal the surface of the base material carrying the active substance by protective coating or lamination.

In this way, even active substances which would otherwise vaporize in the environment of use can be effectively inhibited by the above techniques.

Moreover, among active substances which vaporize at atmospheric temperature, there are substances which are still in a precursor condition but are rendered vaporizable on contact with an appropriate reagent (a decomposition accelarator, a reaction accelerator, etc.) and such substances also fall within the purview of the present invention.

The tape 1 is preferably provided as accommodated in a casette case or in a form which can be accommodated in a casette case. In such a form, the used tape 1 may be easily replaced with a new tape of the same type or a tape 1 carrying a different active substance, thus adding to the market value of the whole apparatus.

The tape 1 may be a disposable tape which is not supplemented with the active substance and particularly when the tape 1 is an endless tape, it may be so arranged that the tape 1 travels through a tank containing the active substance or contacts a foam plastic or interlaced fiber element saturated with the active substance so that the active substance may be constantly or intermittently replenished.

The tape 1 may be so constructed that it carries active substances having different functions in discrete zones along its length. As an alternative, the tape 1 may be provided with a plurality of parallel lanes carrying active substances having different functions. The term 'different functions' as used herein covers the use of different active substances or the use of a given substance in different concentrations. When a plurality of active substances having different functions are supported in discrete zones along the length of the tape 1, the active substance or substances having different functions are sequentially vaporized with the progress of time. On the other hand, when a plurality of active substances or a given active substance in different concentrations is supported in different lanes, one may shift the position of the head 2 relative to the tape 1 or vice versa either manually or by means of a suitable controlling device so as to vaporize any one of the functionally variegated active substance or substances at a desired time or two or more of the functionally variegated active substance or substances concurrently.

The latter arrangement is particularly advantageous when high-quality perfumes or perfumes for aroma therapy are supported, a compound aroma suitable for the atmosphere or for therapeutic purposes can be created.

When active substances having different functions are supported in discrete zones along the length of the tape 1 or in discrete lanes of the tape 1, it is possible, for example, to disinfect a library with formalin, then catch the formalin with ammonia and finally catch the ammonia with a deodorant, all in a series of events overnight.

Thus, the above arrangements assure the vaporization of active substances in a serial fashion.

Head

The head 2 is adapted to release the active substance from the above-mentioned condition in which the vaporization thereof is inhibited, either thermally, physically or chemically. Among such means are those utilizing photochemical reactions.

When the active substance is one that vaporizes under heating, a heating system is employed at the head 2. Such heating system may for example be a thermoelectric system, a hot gas projection system, an infrared or far-infrared radiation system, an electromagnetic heating system, an ultrasonic heating system, a microwave heating system, a heating system utilizing the heat of oxidation or hydration, a laser beam heating system or a heating system utilizing a semiconductor element.

When the active substance is one that vaporizes at ambient temperature, the head 2 is provided with a mechanism adapted to destroy the vaporization-preventing system such as the above-mentioned protective coat or laminate or the capsule or microcapsule wall. As such mechanism for destruction, there may be employed a compressive destruction system, a scratching system, a needle puncture system, a heat melting system, a dissolution system, a photochemical destruction system, and so on. When the active substance is one that is vaporizable at ambient temperature upon contact with a reactant, a suitable system for exposing the active substance to the reactant is employed.

Drive means

The above-mentioned tape 1 is caused to travel relative to the head 2. The term 'relative' as used herein covers all of the case of driving the tape 1 with the head 2 kept stationary, the case of driving the head 2 with the tape 1 kept stationary, and the case of driving both the head 2 and tape 1. It also means the case in which the tape 1 is driven in its longitudinal direction and the head 2 is shifted in the crosswise direction of the tape 1.

As the drive means, one may employ any of the following arrangements, for instance. (1) The tape 1 wound on a supply reel 4 is paid out and taken up on a takeup reel 5, with either the supply reel 4 or the takeup reel 5 or both being driven. (2) The tape 1 is caused to travel by pulling it by means of a drive roll 6. (3) The tape 1 is caused to travel by means of a drive belt 15 driven in contact with the tape 1. It is also possible to set the tape 1 on a reel and pay it out under its own weight while the reel is driven. Systems for driving the head 2, instead of the tape 1, may also be employed.

As a drive source, an electric motor, a recoil spring, gravity, etc. can be utilized.

Others

In the apparatus according to the present invention, a fan may be installed in a suitable position for the purpose of promoting the vaporization of the active substance and/or carrying the vaporized active substance farther.

Thus, in accordance with the present invention, the following effects and advantages are realized.

As the tape 1 is driven relative to be head 2, the active substance carried by the tape 1 is vaporized in the position where the tape 1 contacts or approaches the head 2. Since the tape 1 travels relative to the head 2, the fresh substance is successively supplied to the zone of the head 2 so that the vaporization of the active substance at a constant rate is assured irrespective of the time phase after initiation of the operation.

The temperature distribution of the tape 1 in the vicinity of the head 2 is nearly constant, with the result that even when the active substance is actually a mixture of substances which vaporize under heating, the substances are vaporized according to the temperature distribution so that, unlike in the case of the conventional electric mosquito mat, the variation in vaporized active substances owing to overheating is avoided.

Furthermore, the rate and amount of the active substance can be freely varied by controlling the length of the tape 1, the supply of the active substance to the tape 1, the relative speed of the tape 1 with respect to the head 2, and/or the conditions for removing the control or inhibition of vaporization at the head 2.

With a timer installed, the vaporization of active substances can be made continuous or intermittent as desired or be initiated and completed at preset times.

When an active substance in different concentrations or a plurality of active substances having different functions are carried or supported in discrete zones along the length of the tape 1 or in different lanes of the tape 1, the functionally variegated active substance or substances can be vaporized in sequence or two or more of the different active substances can be vaporized substantially concurrently to provide a compound aroma.

Furthermore, in such an arrangement, one may utilize the present invention in such a manner that the active substance vaporized later acts on the active substance vaporized earlier.

The apparatus according to the present invention is compact and the convenience in use is further enhanced when the tape 1 is accommodated in a casette case.

In addition to the above meritorious features and advantages, the apparatus according to the present invention has many novelty features which make it very attractive to the prospective customers.

The following examples are further illustrative of the method and apparatus according to the present invention.

EXAMPLES

(A) Apparatus Examples

Apparatus Example 1

Figure 1:
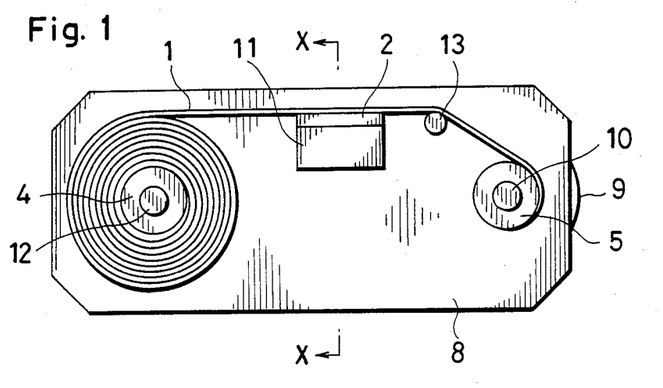
FIG. 1 is a front view showing an embodiment of the apparatus according to the present invention.
Figure 2:
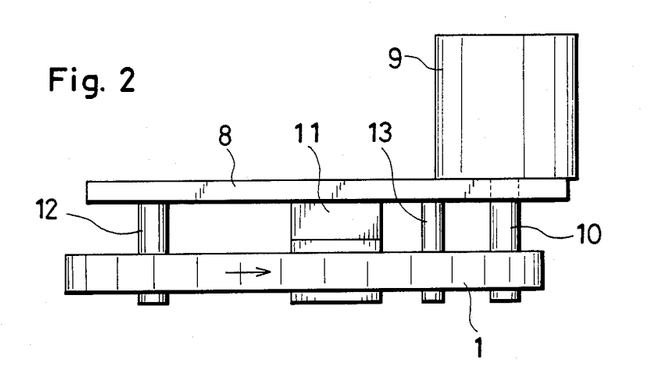
FIG. 2 is a plan view thereof.
Figure 3:
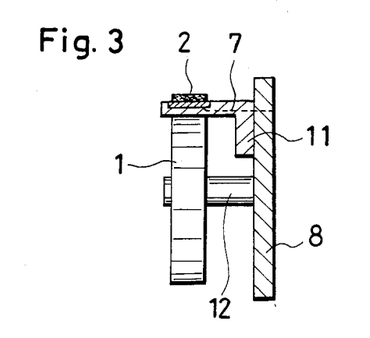
FIG. 3 is a sectional view taken along the axis X—X of FIG. 1.

FIG. 1 is a front view showing an embodiment of the present invention, FIG. 2 is a plan view thereof, and FIG. 3 is a view taken along the line X—X of FIG. 1.

The reference numeral 8 represents a base plate, 9 a reducer-motor mounted on said base plate 8, and 10 a rotary shaft of said reducer-motor 9.

Indicated at 2 is a head which is rigidly mounted on said base plate 8 by a holder 11. The broken line in FIG. 3 shows an electrical wiring 7 for heating the head 2.

The reference numeral 12 represents a supply reel shaft projecting from said base plate 8, and 13 a rotatable guide roll which is also projecting from said base plate 8.

The reference numeral 1 represents a continuous tape comprising a base material carrying an active substance to be vaporized. A supply reel is indicated at 4 and a takeup reel at 5.

The continuous tape 1 is wound around said supply reel 4. The tape 1 carries an adhesive at its free end so that the tape 1 paid out from the supply reel 4 may be adhered to the periphery of the takeup reel 5.

As the reducer-motor 9 is started and its drive shaft 10 revolves, the takeup reel 5 begins to revolve so that the tape 1 is paid out from the supply reel 4, guided by said guide roll 13 and taken up on the takeup reel 5. In the course of travel of the tape 1, the active substance carried by the tape 1 is vaporized in the position where it contacts the head 2 or in the vicinity thereof.

Apparatus Example 2

Figure 4:
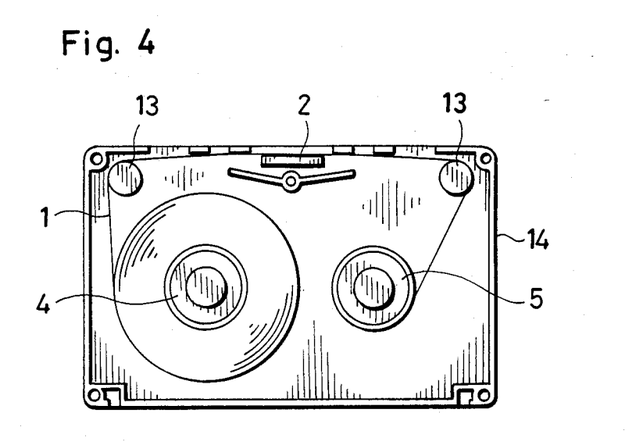
FIG. 4 is a schematic view showing the main components of another embodiment of the apparatus according to the present invention.

FIG. 4 is a schematic view showing the main components of another embodiment of the apparatus according to the present invention. In this embodiment, the tape 1 is provided as packaged in a casette case. Indicated at (14) is a casette case body, on which a cover (not shown) can be snugly fitted. The reference numeral 4 represents a supply reel, 5 a takeup reel, and 13 a guide roll. The reference numeral 1 represents a tape which is paid out from said reel 4 and taken up on a takeup reel 5. Indicated at 2 is a head.

The casette case containing the tape 1 is loaded into the body of the apparatus equipped with a drive mechanism and a head and its associated components (only the head is shown) and the takeup reel 5 is driven as in the foregoing embodiments, whereupon the tape 1 is paid out from the supply reel 4 and taken up on the takeup reel 5. In the course of travel of the tape 1, the active substance carried by the tape 1 is vaporized in the position where the tape contacts the head 2 or in the vicinity thereof.

Apparatus Example 3

Figure 5:
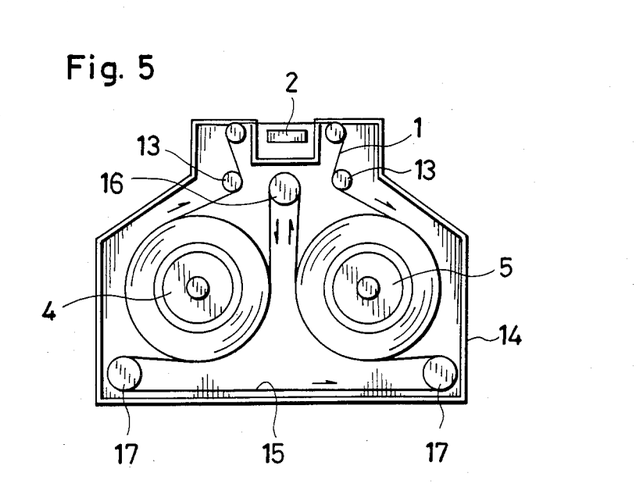
FIG. 5 is a schematic view showing a still another embodiment of the apparatus according to the present invention.

FIG. 5 is a schematic view showing the main components of still another embodiment of the present invention. In this embodiment, a tape 1 is provided as packaged in a casette case. Indicated at (14) is a casette case body, on which a cover (not shown) can be snugly fitted. The reference numeral 15 represents a rubber belt, and 16 a drive roller. Guide rollers for said rubber belt 15 are indicated at 17.

The reference numeral 4 represents a supply reel, 5 a takeup reel and 13, 13 guide rollers. Indicated at 1 is a tape which is paid out from said supply reel 4 and taken up on said takeup reel 5. The reference numeral 2 represents a head.

As the drive roller 16 is driven, the rubber belt 15 runs at a constant speed and the tape 1 in contact with the rubber belt 15 also runs following the belt 15 so that the tape 1 is paid out from said supply reel 4 and taken up on said takeup reel 5.

In the course of travel of the tape 1, the active substance carried by the tape 1 is vaporized in the position where the tape 1 contacts the head 2 or in the vicinity thereof.

Apparatus Example 4

Figure 6:
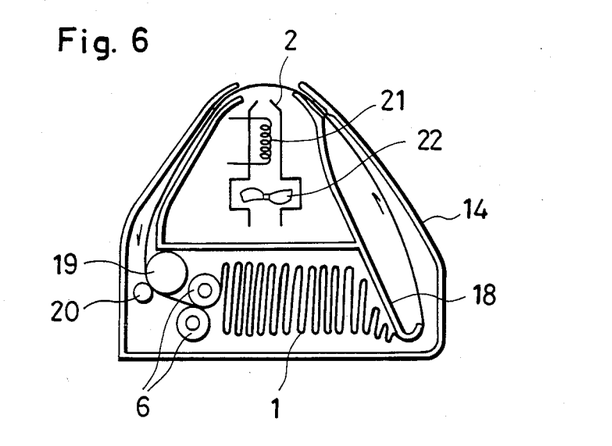
FIG. 6 is a schematic view showing another yet embodiment of the apparatus according to the present invention.

FIG. 6 is a schematic view showing the main components of another yet embodiment of the apparatus according to the present invention. In this embodiment, an endless tape 1 is supplied as packaged in a casette case. Indicated at (14) is a casette case body, on which a cover (not shown) can be snugly fitted. This apparatus includes a pair of drive rollers 6, 6 and a guide plate 18. The tape 1 travels smoothly as it is simply pulled by said pair of drive rollers.

The reference numeral 19 represents a rotary unit for providing the endless tape with a supplemental supply of the active substance to be vaporated. Indicated at 20 is a retaining roller. The numeral 2 represents a head, 21 a heating means for the head 2, and 22 a fan for directing a heated air away from the tip of the head 2.

As said drive rollers 6, 6 are driven, the tape 1 is caused to travel and the active substance carried thereby is vaporized in the position where the tape 1 contacts the head 2 or in the vicinity thereof. The tape 1 is provided with an additional supply of the active substance as it contacts the rotary unit 19.

Experimental Example (B)

Experimental Example 1

A vaporization test was performed using the apparatus illustrated in FIGS. 1 through 3.

The dry-distillate prepared by subjecting dried tea leaf to dry distillation in a vacuum of 20 mmHg and collecting the fraction boiling at 180° to 200° C. was dissolved in 5 volumes of propylene glycol-water to give a solution. Polyester fiber felt tape with a length of 1 m, a width of 10 mm, a thickness of 1 mm and a weight of 250 g/m² was impregnated with the above solution at the rate of 40 g/m² to give a tape 1.

The tape-driving rate of the takeup reel was set at 10 cm/hour and a thermoelectric head 2 was set at a heating temperature of 150° C.

During an experimental period of 10 consecutive hours, the rate of vaporization of tea leaf dry-distillate was constant throughout so that the unpleasant odor in the room could be effectively eliminated.

Experimental Example 2

The test procedure of Experimental Example 1 was repeated except that an insectidal composition consisting of 90 weight % of allethrin and 10 weight % of piperonyl butoxide was dissolved in water-ethanol and a felt tape was impregnated with the solution. However, in this experiment, an aromatic polyamide felt was used in place of the polyester fiber felt and the tape-driving speed of the takeup reel was set at 10 cm/hour and the heating temperature of the head 2 was set at 200° C.

Throughout the experimental period of 10 consecutive hours, the rate of vaporization of the insecticidal agent was constant.

Experimental Example 3

A vaporization test was carried out using the apparatus of FIG. 4.

Orange, lemon and lavender oils were respectively mixed with a 2 weight % solution of carrageenan in water and each mixture was coated on one side of a 40μ-thick polyester film in 3 zones. After drying the coated side of the film was sprayed with a protective film forming-acrylic emulsion and dried. The dried film was cut across the zones to provide 8 mm-wide tapes.

A vaporization test with the tape prepared in the above manner was carried out under the same conditions as described in Experimental Example 1. However, the tape-driving speed of the takeup reel 4 was set at 10 cm/hour, and as the head 2, a scratching system head for breaking the protective coat was employed.

During the experimental period of 10 consecutive days, the aroma generated changed from orange to lemon to lavender with lapse of the time.

Experimental Example 4

Figure 7:
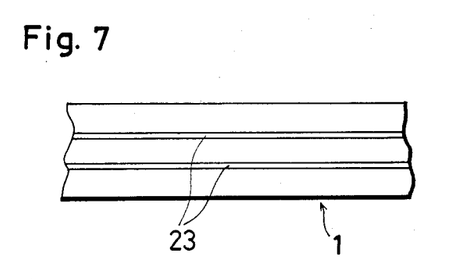
FIG. 7 is a segmental view showing an example of the tape.

The test procedure of Experimental Example 3 was repeated except that the apparatus shown in FIG. 5 and the tape 1 illustrated in FIG. 7 were used. Referring to FIG. 7, the tape 1 has three parallel lanes with a silicone water-repellent agent applied to form a borderline 23 between lanes, said lanes being coated with liquid compositions based on orange, lemon and lavender essential oils, respectively, and further coated with a protective coating composition.

In this experiment, the head 2 was shifted from a position corresponding to one of said three lanes to another position facing the next lane at appropriate time intervals, whereby the various aromas could be selectively generated as desired.

Experimental Example 5

A vaporization test was carried out using the apparatus of FIG. 6.

As the tape 1, the same tape carrying a tea leaf dry-distillate as the one used in Experimental Example 1 was employed. The tape-driving speed of the drive rollers 6, 6 was set at 10 cm/hour, and as the head 2, a hot air projection type head using a nicrome wire as heating means 21 was employed. The temperature of hot air was set at 180° C. As the rotary unit 19 for a supplemental supply of the active substance to be vaporized, a cylindrical element of polyurethane sponge saturated with the same substance as above was used.

Throughout the experiment period of 3 consecutive days, the rate of vaporization of the tea leaf dry-distillate was constant. This apparatus can be used for a very long time only if the rotary unit 19 is supplied with the substance from time to time.

What is claimed is:

1. A method of vaporizing active substances which comprises driving a tape comprising a base material and, as carried thereon, at least one active substance which vaporizes at ambient temperature or under heating in a condition in which the vaporization thereof is inhibited relative to a head adapted to remove the inhibition of vaporization to thereby vaporize said active substance in a position where said tape contacts or approaches said head.

2. A method of vaporizing active substances as claimed in claim 1 wherein said active substance is a member selected from the group consisting of deodorants, aromas, antimicrobial agents, insect control agents, air fresheners, attractants, repellents, rust inhibitors, spoilage control agents, drugs for absorption from the respiratory organ, skin or mucosa, and presence effect aromas.

3. A method of vaporizing active substances as claimed in claim 2 wherein said aromas are scents, phytoncides or aromas for aroma therapy.

4. A method of vaporizing active substances as claimed in claim 1 wherein the inhibition of vaporization is removed thermally.

5. A method of vaporizing active substances as claimed in claim 1 wherein the inhibition of vaporization is removed physically.

6. An apparatus for vaporizing active substances which comprises a tape comprising a base material and, as carried thereon, at least one active substance which vaporizes at ambient temperature or under heating in a condition in which the vaporization thereof is inhibited, a head adapted to remove the inhibition of vaporization thermally, physically or chemically, and a drive means adapted to drive said tape relative to said head.

7. An apparatus for vaporizing active substances as claimed in claim 6 wherein said tape is accommodated or accommodatable in a casette case.

8. An apparatus for vaporizing active substances as claimed in claim 6 wherein said tape is non-endless.

9. An apparatus for vaporizing active substances as claimed in claim 6 wherein said tape is endless.

10. An apparatus for vaporizing active substances as claimed in claim 6 wherein said tape is one not to be supplemented with said active substance.

11. An apparatus for vaporizing active substances as claimed in claim 6 wherein said tape is one that can be supplemented with said active substance.

12. An apparatus for vaporizing active substances as claimed in claim 6 wherein said drive means includes a supply reel and a takeup reel, whereby said tape is paid out from said supply reel and taken up on said takeup reel.

13. An apparatus for vaporizing active substances as claimed in claim 6 wherein said drive means includes a drive roll by which said tape is driven relative to said head.

14. An apparatus for vaporizing active substances as claimed in claim 6 wherein said drive means includes a drive belt driven in contact with the tape, whereby said tape is driven relative to said head.

15. An apparatus for vaporizing active substances as claimed in claim 6 wherein said tape has an active substance or substances with variegated functions as supported on the base material thereof.

16. An apparatus for vaporizing active substances as claimed in claim 6 wherein said tape has an active substance or substances with variegated functions as supported on the base material thereof in a plurality of lanes.

* * * * *